United States Patent [19]

Wan et al.

[11] 4,201,638

[45] May 6, 1980

[54] TRIPLE IONS OF 1,2- AND 1,4-DICARBONYL COMPOUNDS AND ANALOGS THEREOF CONTAINING NITROGEN AND CONTAINING TWO STRATEGIC OXYGEN OR NITROGEN GROUPS AND PROCESS FOR PRODUCING SAME

[75] Inventors: Jeffrey K. S. Wan, Kingston; Kuang S. Chen, Amherstview, both of Canada

[73] Assignee: Queen's University at Kingston, Kingston, Canada

[21] Appl. No.: 945,627

[22] Filed: Sep. 25, 1978

[51] Int. Cl.$^2$ .............................. B01J 1/10; B01J 1/12; C07G 13/00; C07C 107/02
[52] U.S. Cl. ..................... 204/158 R; 204/158 HE; 260/192; 260/347.8; 260/369; 260/396 R; 260/396 N; 260/464; 260/465.5R; 568/716; 544/336; 260/65 R; 260/346.11; 528/225; 260/465.5 R; 568/716
[58] Field of Search ............... 260/192, 347.8, 621 P, 260/464, 465.5, 369, 396 R, 396 N; 204/158 R, 158 HE; 544/336

[56] References Cited

U.S. PATENT DOCUMENTS

| | | | |
|---|---|---|---|
| 2,661,354 | 12/1953 | Schmidle | 260/347.8 |
| 3,595,922 | 7/1971 | Manos | 260/347.8 X |

OTHER PUBLICATIONS

Mauser et al., Zeit. Fur Naturforschung, vol. 276, pp. 1354-1359, (1972).
Vlasova et al., Chemical Abstracts, vol. 70, Item #15301t, (1969).
Brandon et al., J. Chem. Soc., (London), vol. of 1961, pp. 4273-4280.
Harada et al., Bull. Chem. Soc., Japan, vol. 34, pp. 585-586, (1961).

Primary Examiner—Floyd D. Higel
Attorney, Agent, or Firm—Richard J. Hicks; Stanley E. Johnson

[57] ABSTRACT

Stable paramagnetic alkali radical cationic triple ions of selected 1,2 and 1,4 dicarbonyl compounds and their nitrogen-containing analogs have been produced by both conventional alkali metal reduction of an appropriate organic compound and by a novel process in which the selected 1,2 or 1,4 dicarbonyl compound or the nitrogen containing analog thereof is mixed with an alkali tetraphenylborate and irradiated under ultraviolet light.

6 Claims, No Drawings

TRIPLE IONS OF 1,2- AND 1,4-DICARBONYL COMPOUNDS AND ANALOGS THEREOF CONTAINING NITROGEN AND CONTAINING TWO STRATEGIC OXYGEN OR NITROGEN GROUPS AND PROCESS FOR PRODUCING SAME

This invention relates to stable alkali radical triple ions of 1,2 and 1,4-dicarbonyl compounds and analogs thereof containing nitrogen containing two strategic oxygen or nitrogen atoms and to a novel process for producing them.

Alkali radical ion pairs, triple ions and ion quadruplets are known, per se, to the art. Earlier investigation of cationic triple ions have, however, mainly centered around radical anion systems having two polar groups in an axially symmetrical position, i.e. the 1,4-semiquinones and the pyrazines. Such triple ions as have been made have generally been produced by alkali metal reduction, under vacuum—a tedious process which requires purification of absolutely dried solvent and the operation of high vacuum line apparatus. Not only are such triple ions relatively unstable, but the coordination power of the metal is not very strong and the various counter cations in the triple ions are limited due to the reduction potential of the compounds.

Generally, triple ions of the prior art have been prepared by a two stage process: (a) alkali metal reduction followed by the addition of an alkali metal tetraphenylborate or (b) addition of alkali metal tetraphenyl-borate followed by the alkali metal reduction. For example:

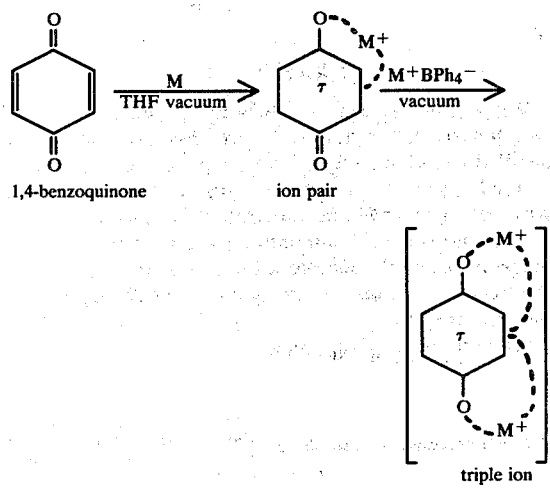

1,4-benzoquinone     ion pair triple ion

The first step leading to an ion pair is well known among such 1,2- and 1,4-dicarbonyl compounds as benzil, 9,10-phenanthrene-quinone, acenaphthenequinone and transoxindigo, but addition of an alkali metal salts, such as $NaBPh_4$, does not result in the second step, namely the formation of the triple ion. It has now been found, however, that 1,2 and aliphatic 1,4 substituted diketones with carbonyl groups strategically placed near the "ethereal oxygens" such as furil (1,2 diketone) and di-tert-butyl azodicarboxylate (BADC - a 1,4-diketone) readily interact with $MBPh_4$ to form the corresponding triple ions. Similar results are also obtained with the nitrogen analogs i.e. pyrazines and tetracyano compounds. An interesting property of such triple ions is that they are paramagnetic and consequently of interest, among other uses, for incorporation into heretofore non-conducting polymers, such as polyethylene, to produce a conducting polymer. Considerable effort has been expended in the past in the search for a conducting or semi-conducting polymer without significant success. In this regard attention is directed to Canadian Pat. No. 729,650 issued Mar. 8, 1966 to Wahlig and assigned to E. I. du Pont de Nemours and Company wherein there is described the production of a salt $M^+A^{-\cdot-}M^+$ in which $M^+$ is an organic cation (not an alkali metal) and A is a tetracyanoquinodimethan moiety or alkyl substituent thereof, for use as a film type semi-conductor. It will, of course be appreciated that this salt is an ion pair and not a triple ion, which in the present specification, is defined as containing two alkali cations and one organic radical anion thus producing a triple ion with a net positive charge. Also as used herein the term alkali cation is to be construed as including the alkali metals such as lithium, sodium and potassium, and also ammonium which heretofore has not been considered suitable for the production of triple ions.

Thus, it is an object of the present invention to provide a novel series of stable, paramagnetic alkali radical triple ions which may be used as a polymerization promoter and incorporated into the polymer. Other uses of the triple ions of the present invention include use as a complexing or chelating agent particularly for Group IVB metals contained in organometal salts thereof.

Another object of the present invention is to provide a novel photochemical process for producing triple ions.

Thus, by one aspect of this invention there is provided a stable, paramagnetic, alkali radical triple ion of compounds selected from the group consisting of 1,2 and 1,4-dicarbonyl compounds and analogs thereof containing nitrogen containing two strategic oxygen or nitrogen atoms.

By another aspect of this invention there is provided a process for the production of triple ions of 1,2 and 1,4-dicarbonyl compounds and analogs thereof containing nitrogen comprising mixing said compound with an alkali organo salt and irradiating the mixture with radiations in the range between about 300 and 500 Nm.

The invention will be described in more detail hereinafter by reference to the specific examples.

As noted above, triple ions have heretofore been produced by alkali metal reduction under vacuum, and indeed the present inventors first produced their novel triple ions in the conventional manner. It was discovered however that when solutions, generally but not essentially tetrahydrofuran (THF), containing either furil or di-tert-butylazodicarboxylate (BADC) in the presence of $Na^+BPh_4^-$ or similar alkali tetraphenylborate salt where photolysed, the identical furil or BADC sodium or other alkali triple ion was obtained. Photolysis may be conducted at any suitable frequency range, between about 300 and 500 Nm. Although frequencies below 300 Nm may be employed with excellent results, it is necessary to employ special quartz equipment which is extremely costly relative to the standard Pyrex ® glass hardware which may be used in the preferred range. Radiations between about 400 and 500 Nm are visible to the naked eye and above about 500 Nm are not particularly suitable. The preferred range is in the near U-V range of 300–400 Nm.

I. Photochemical preparation of Triple Ions (a) 1,2-Dicarbonyl Compounds Such as Furil

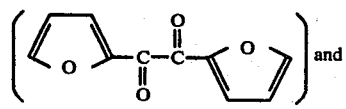 and 2,2'-pyridil 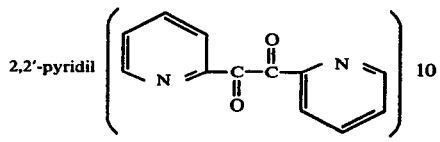

EXAMPLE I 1.14 mg of Furil and 4.05 mg of ammonium tetraphenylborate were dissolved in 0.2 ml distilled THF. The sample solution was placed in a 2.5 mm i.d. Suprasil ® tube and deoxygenated by purging with nitrogen gas. The tube was then placed in an electron spin resonance cavity and irradiated by a 1000 W super pressure mercury lamp. The almost immediate formation of ammonium furil triple ion was confirmed by electron spin resonance spectroscopy.

(b) 1,4-Dicarbonyl Compounds

Di-t-butyl Azodicarboxylate 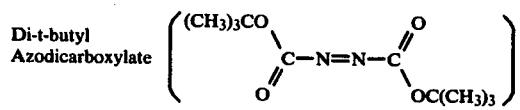

EXAMPLE 2

1.38 mg of Di-t-butyl azodicarboxylate and 3.91 mg of lithium tetraphenylborate were dissolved in 0.2 ml distilled tetrahydrofuran. The sample solution contained in a 2.5 mm i.d. pyrex tubing was deoxygenated by purging with nitrogen gas. The electron spin resonance spectrum of lithium di-t-butylazodicarboxylate, triple ions was recorded when the sample solution was irradiated in an electron spin resonance cavity by a 1000 W super pressure mercury lamp.

(c) 1,4-Quinones

Anthraquinone 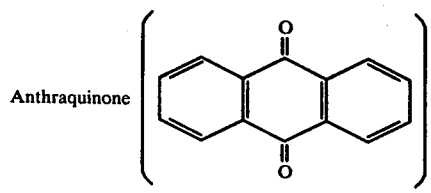

Quinizarin 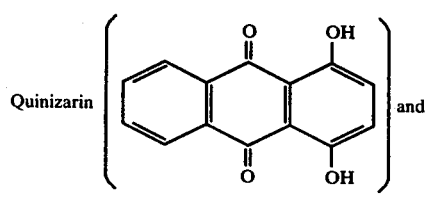 and

Duroquinone 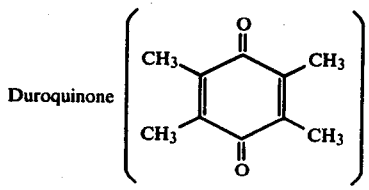

EXAMPLE 3

1.25 mg of Anthraquinone and 4.11 mg of sodium tetraphenylborate were dissolved in 0.2 ml distilled tetrahydrofuran. The sample solution contained in a 2.5 mm i.d. pyrex tubing was deoxygenated by purging with nitrogen gas. The electron spin resonance spectrum of sodium anthraquinone triple ions was recorded when the sample solution was irradiated on an electron spin resonance cavity by a 1000 W super pressure mercury lamp.

(d) Pyrazines

Pyrazine 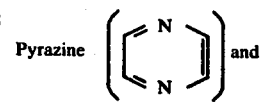 and tetramethylpyrazine 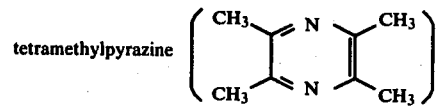

EXAMPLE 4

0.48 mg of pyrazine and 6.74 mg of tetra-n-butylammonium tetraphenylborate were dissolved in 0.2 ml distilled tetrahydrofuran. The sample contained in a 2.5 mm i.d. pyrex tubing was deoxygenated by purging with nitrogen gas. The electron spin resonance spectrum of tetra-n-butylammonium pyrazine triple ions was recorded when the sample solution was irradiated in an electron spin resonance cavity by a 1000 W super pressure mercury lamp.

(e) Tetracyano Compounds 7,7,8,8-Tetracyanoquinodimethane 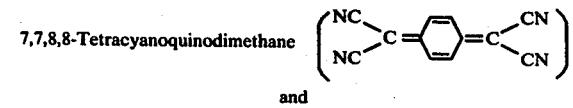

and

Tetracyanoethylene 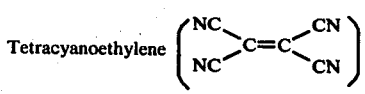

EXAMPLE 5

1.23 mg of 7,7,8,8-Tetracyanoquinodimethane and 4.30 mg of potassium tetraphenylborate were dissolved in 0.2 ml distilled tetrahydrofuran. The sample solution contained in a 2.5 mm i.d. pyrex tubing was deoxygentated by purging with nitrogen gas. The electron spin resonance spectrum of potassium 7,7,8,8-tetracyanoquinodimethane triple ions was recorded when the sample solution was irradiated in an electron spin resonance cavity by a 1000 W super pressure mercury lamp. As noted hereinbefore, triple ions of the present invention may be employed as polymerization promoters or catalysts and incorporated into the polymer structure. The precise mechanism of incorporation is not yet fully understood but it is believed that the triple ions are incorporated directly into the main or backbone structure of the polymer and serve to impart paramagnetic properties to the polymer.

II. Polymerization of Tetrahydrofuran by Boron Trifluoride in the Presence of Triple Ions

EXAMPLE 6

38.04 mg of furil and 136.89 mg of sodium tetraphenylborate were placed in a 10 mm o.d. pyrex tubing with a side arm containing sodium metal. This sample tubing was connected to a high vacuum line, and degassed to a residual pressure of $10^{-4}$ mm Hg. The sodium metal was sublimated into the sample tubing and formed a clean sodium mirror. A 2.0 ml of absolutely dried tetrahydrofuran was transferred into the sample tubing via vacuum line. After the contact of the sample solution with the sodium mirror, the left-over sodium mirror was sealed off. The blue tetrahydrofuran solution of sodium furil triple ions was confirmed by electron spin resonance spectroscopy. 271.24 mg of boron trifluoride treated with sodium fluoride was transferred into the blue tetrahydrofuran solution of sodium furil triple ions. A green polymer was formed. The composition of the sample solution and the physical properties of the green polymers are listed below.

COMPOSITION OF SAMPLE SOLUTION

| Furil | 0.0002 mole | 0.1 M |
|---|---|---|
| Sodium Tetraphenylborate | 0.0004 mole | 0.2 M |
| Boron Trifluoride | 0.0004 mole | 2.0 M |
| Tetrahydrofuran | 0.0246 mole | 12.3 M |

PHYSICAL PROPERTIES OF GREEN POLYMER

1. Electron Spin Resonance: A broad signal
2. Reversibility of Polymerization: Yes
3. Conductivity: Not yet available
4. Molecular weight: 200,000.

EXAMPLE 7

The procedure of example 6 was repeated, except that sodium di-t-butylazodicarboxylate triple ion was used instead of the sodium furil triple ion. A pale yellow tetrahydrofuran polymer was formed with similar properties to those of the green polymer.

EXAMPLE 8

III. Polymerization of Tetrahydrofuran and/or 7,7,8,8-Tetracyanoquinodimethane in the Presence of Triple Ions 5 mg of 7,7,8,8-Tetracyanoquinodimethane and 5 mg of tetra-n-butylammonium tetraphenylborate were placed on a 2.5 mm i.d. pyrex tube which was connected to a vacuum line. After the pressure of the sample tube was down to $10^{-4}$ mm Hg, 0.2 ml of absolutely dried and deoxygenated tetrahydrofuran was transferred into the sample tube via the vacuum line. An electron spin resonance spectrum of tetra-n-butylammonium 7,7,8,8-tetracyanoquinodimethane triple ions was recorded after irradiation with light from a high pressure 200 W mercury lamp.

The solution was placed on an ice-water bath with room light. A suspended material was noticed with an increase of viscosity of the sample solution. The viscosity of the solution can be lowered by raising the temperature, and this process is reversible.

A further use for the triple ions of the present invention is that of a complexing or chelating agent of considerable power. It has been found that in all cases the sodium triple ion is the most stable. Thus, the addition of $Na^+BPh_4^-$ to either the ion-pair or the triple ion of another type of alkali ion will lead to spontaneous exchange always resulting in the formation of sodium triple ions. For the furil system, the K triple of ion was found to be more stable than the Li and in the BADC system the Li triple ion was more stable. Such orders of stability allow a high degree of selectivity in triple ion formation when more than one type of alkali cations are present and may have considerable significance in biological systems in which K triple ions can enter a cell and exchange with $Na^+$ ions in the cell before leaving as the Na triple ion. It has been found that 18-crown-6 polyether, which heretofore has been considered one of the most powerful complexing reagents for metal ions known, is not capable of decomplexing the triple ions of the present invention. The remarkable complexing properties of the present triple ions relative to the so-called crown-ethers suggests the use thereof as complexing reagents for heavy metals. As will be appreciated heavy metals, of the Group IVB type, are generally found in biological systems in the form of organo metal salts and for this reason the present triple ions have been reacted with various organo metallic salts containing mercury, lead and tin.

EXAMPLE 9

IV. Ion Exchange Reaction of Triple Ions with Group IVB Organo Metallic Salts

A 2.0 ml THF solution of $10^{-3}$ M sodium furil triple ions was brought into contact with 7.7 mg of triphenyltinchloride, and the product was examined by electron spin resonance spectroscopy. A triphenyltin spin adduct of furil was recorded.

We claim:

1. A stable, paramagnetic alkali radical triple cationic ion of a compound selected from the group consisting of furil, pyridil, di-tert-butylazodicarboxylate, anthraquinone, quinizarin, duroquinone, pyrazine, tetramethyl pyrazine, tetracyanoquinodimethane, and tetracyanoethylene.

2. A triple ion as claimed in claim 1 wherein said alkali radical is selected from the group consisting of ammonium, lithium, sodium and potassium.

3. A process for producing stable paramagnetic alkali radical cationic triple ions of a compound selected from the group consisting of furil, pyridil, di-tert-butylazodicarboxylate, anthraquinone, quinizarin, duroquinone, pyrazine, tetramethyl pyrazine, tetracyanoquinodimethane, and tetracyanoethylene comprising mixing said compound with an alkali tetraphenylborate in an organic solvent therefor and irradiating the resultant mixture with radiations in the range between about 300 and 500 Nm.

4. A process as claimed in claim 3 wherein said radiations are in the range between 300 and 400 Nm.

5. A process as claimed in claim 4 wherein said alkali radical is selected from the group consisting of ammonium, lithium, sodium and potassium.

6. A process as claimed in claim 3 wherein said organic solvent is tetrahydrofuran.

* * * * *